United States Patent [19]
Maclaren et al.

[11] Patent Number: 6,066,475
[45] Date of Patent: May 23, 2000

[54] PARATHYROID CYTOSOLIC AUTOANTIGENS RECOGNIZED BY AUTOANTIBODIES FROM PATIENTS WITH ACQUIRED HYPOPARATHYROIDISM

[75] Inventors: Noel K. Maclaren, Archer; Yao-Huo Song, Gainesville, both of Fla.

[73] Assignee: University of Florida, Gainesville, Fla.

[21] Appl. No.: 08/991,922

[22] Filed: Dec. 16, 1997

Related U.S. Application Data

[62] Division of application No. 08/519,905, Aug. 28, 1995, Pat. No. 5,723,343.

[51] Int. Cl.$^7$ .............................. C12P 21/00; C12N 1/14; C12N 1/20; A61K 38/00
[52] U.S. Cl. ........................ 435/69.3; 435/455; 435/471; 435/325; 435/252.3; 435/255.1; 530/324; 530/412
[58] Field of Search .................................. 435/69.3, 455, 435/471, 325, 252.3, 255.1; 530/324, 412

[56] References Cited

U.S. PATENT DOCUMENTS

| | | |
|---|---|---|
| 4,864,020 | 9/1989 | Cance et al. . |
| 5,053,491 | 10/1991 | Cance et al. . |

FOREIGN PATENT DOCUMENTS

| | | |
|---|---|---|
| 8803271 | 5/1988 | WIPO . |
| 9415214 | 7/1994 | WIPO . |
| 9425604 | 11/1994 | WIPO . |
| 9428019 | 12/1994 | WIPO . |

OTHER PUBLICATIONS dela Cruz et al Vaccines 91. pp. 345–349. 1991.
Lazar et al. Molecular and Cellular Biology. Mar. 1988 vol. 8: No. 3 pp. 1247–1252.
Conklin, B.R., H.R. Bourne (1994) "Marriage of the flytrap and the serpent" Nature 367:22.
Lund, B.J., et al. (1980) Vitamin D Metabolism in Hypoparathyroidism Jouranl of Clinical Endocrinology and Metabolism 51(3):606–610.
Aurbach, G.D., S.J. Marx, A.M. Spiegel (1990) "Parathyroid Hormone, Calcitonin, and the Calciferols" Williams Textbook of Endocrinolgoy 8:1397–1476.
Neufeld, M., N. Maclaren, R. Blizzard (1980) "Autoimmune Polyglandular Syndrome" Pediatric Annals 9(4):154–162.
Neufeld, M. N.K. Maclaren, R.M. Blizzard (1981) "Two Types of Autoimmune Addison's Disease Associated with Different Polyglandular Autoimmune (PGA) Syndrome" Medicine 60(5):355–362.
Winter, W. E., M. Obata, N.K. Maclaren (1992) "Clinical and Molecular Aspects of Autoimmune Endocrine Disease" Clinical and Molecular Aspects of Autoimmune Diseases. Concepts Immunopathol. 8:189–221.
Maclaren, N.K., W.J. Riley (1985) "Thyroid, Gastric, and Adrenal Autoimmune Associated with Insulin–dependent Diabetes Mellitus" Diabetes Care 8(1)34–38.

Muir, A., N.K. Maclaren (1991) "Autoimmune diseases of the Adrenal Glands, Parathyroid Glands, Gonads, and Hypothalamic–Pituitary Axis" Endocrinology and Metabolism Clinics of North America 20(3):619–644.
Ahonen, P. et al. (1988) "The Expression Autoimmune Polyglandular Disease Type I Appears Associated with Several HLA–A Antigens but not with HLA–DR" Clinical Endocrinology and Metabolism 66(6)1152–1157.
Aaltonen, J. et al. (1994) "An autosomal locus causing autoimmune disease: autoimmune polyglandular disease type I assigned to chromosome 21" Nature Genetics 8:83–87.
Ahonen, P. et al. (1990) "Clinical Variation of Autoimmune Polyendocronopathy–Candidiasis–Ectodermal Dystrophy (Apeced) in a Series of 68 Patients" The New England Journal of Medicine 322(26):1829–1836.
Blizzard, R.M. et al. (1966) "The Incidence of Parathyroid and other Antibodies in the Sera of Patients with Idiopathic Hypoparathyroidism" Clin. Exp. Immunol. 1:119–128.
Betterle, C. et al. (1985) "Demonstration and characterization of anti–human mitochondria autoantibodies in idiopathic hypoparathyroidism and in other conditions" Clin. exp. Immunol. 62:353–360.
Brandi, M.–L. et al. (1986) "Autoantibodies cytotoxic to bovine parathyroid cells in autoimmune hypoparathyroidism" Proc. Natl. Acad. Sci. USA 83:8366–8369.
Fattorossi, A. et al. (1988) "Anti–endothelial cell natibodies: Detection and characterization in sera from patients with autoimmune hypoparathyroidism" Proc. Nat. Acad. Sci. USA 85:4015–4019.
Song, Y.–H. et al. (1995) "Acquired Hypoparathyroidism is Associated with Autoantibodies 70 and 80 KDa Parathyroid Specific Proteins as well as 120–140 KDa Calcium Receptor" 77th Annual Meeting of the Endocrine Society, Washington, D.C., Jun. 14–17, 1995, **abstract.
Pollak, M.R. et al. (1993) "Mutations in the Human $Ca^{2+}$–Sensing Receptor Gene Cause Familial Hypocalciuric Hypercalcemia and Neonatal Severe Hyperparathyroidism" Cell 75:1297–1303.
Brown, E.M. et al. (1993) "Cloning and characterization of an extracellular $Ca^{2+}$–sensing receptor from bovine parathyroid" Nature 366:575–580.
Irvine, W.J., L. Scarth (1969) "Antibody to the Oxyphil Cells of the Human Parathyroid in Idiopathic Hypoparathyroidism" Clin. exp. Immunol. 4:505–510.

(List continued on next page.)

*Primary Examiner*—Sheela Huff
*Assistant Examiner*—Geetha P. Bansal
*Attorney, Agent, or Firm*—Saliwanchik, Lloyd & Saliwanchik

[57] ABSTRACT

Disclosed are novel autoantigens and methods useful in the detection of autoantibodies in persons that have developed, or are at risk of developing, autoimmune hypoparathyroidism. The novel autoantigens of the subject invention may be used to achieve early diagnosis and treatment of autoimmune hypoparathyroidism, and possibly other autoimmune diseases which are frequently associated with autoimmune hypoparathyroidism.

6 Claims, 2 Drawing Sheets

OTHER PUBLICATIONS

Juhlin, C. et al. (1987) "Monoclonal antibodies with exclusive reactivity against parathyroid cells and tubule cells of the kidney" Proc. Natl. Acad. Sci. USA 84:2990–2994.

Wilkin, T.J. (1990) "Receptor Autoimmunity in Endocrine Disorders" The New England Journal of Medicine 323(19):1318–1324.

Davies, T.F. (1981) "Autoantibodies to the Human Thyrotropin Receptor Are Not Species Specific" Journal of Clinical Endocrinology and Metabolism 52:426–430.

Gonzalez–Ros, J.M. et al. (1984) "Binding of Anti–Acetylcholine Receptor Antibodies Inhibits the Acetylcholine Receptor Mdiated Cation Flux" Biochemical and Biophysical Research Communicatons 120(2):368–375.

Fumagalli, G. et al. (1982) "Ultrastructural Aspects of Acetylcholine Receptor Turnover at the Normal End–plate and in Autoimmune Myasthenia Gravis" Journal of Neuropathology and Experimental Neurology 41(6):567–579.

Desouki, A. et al. (1981) "A New Mechanaism Revealed for the Action of Antibodies on Acetylcholine Receptor Function" Experimental Neurology 73:440–450.

Loveridge, N. et al. (1980) "Inhibition of parietal cell function by human gammaglobulin containing gastric parietal cell antibodies" Clin. exp. Immunol. 41:264–270.

Kendall–Taylor, P. et al. (1988) "Antibody that blocks stimulation of cortisol secretion by adrenocorticotrophic hormone in Addison's disease" British Medical Journal 296:1489–1491.

Maron, R. et al. (1983) "Autoantibodies to the insulin receptor in juvenile onset insulin–dependent diabetes" Nature 303:817–818.

Wortsman, J. et al. (1992) "T–Lymphocyte Activation in Adult–Onset Idiopathic Hypoparathyroidism" The American Journal of Medicine 92:352–356.

Song, Y.–H. et al. (1994) "The role of tyrosinase in autoimmune vitiligo" The Lancet 344:1049–1052.

Maron, R. et al. (1983) "Autoantibodies to the insulin receptor in juvenile onset insulin–dependent diabetes" Nature 303:817–818.

Wortsman, J. et al. (1992) "T–Lymphocyte Activatiion in Adult–Onset Idiopathic Hypoparathyroidism" The American Journal of Medicine 92:352–356.

Song, Y.–H. et al. (1994) "The role of tyrosinase in autoimmune vitiligo" The Lancet 344:1049–1052.

Leiser, M., L.M. Sherwood (1989) "Calcium–binding Proteins in the Parathyroid Gland" The Journal of Biological Chemistry 264(5):2792–2800.

Jones, K.H. et al. (1963) "Edetic–Acid Test of Parathyroid Insufficiency" The Lancet (Jul. 20, 1963):119–121..

Jones, K.H. et al. (1963) "Prevalence of Parathyroid Insufficiency after Thyroidectomy" The Lancet (Jul. 20, 1963):121–124.

Davis, R.H. et al. (1961) "Prevalence of Parathyroid Insufficiency after Thyroidectomy" The Lancet (Dec. 30, 1961):1432–1435.

Brown, E.M. (1991) "Extracellular $Ca^{2+}$ and other Ions as Extracellular (First) Messengers" Biological Reviews 71(2):371–411.

Li, Yangxin, Yao–Hua Song, Nadeem Rais, Ellen Connor, Desmond Schatz, Andrew Muir, Noel Maclaren (1996) "Autoantibodies to the Extracellular Domain of the Calcium Sensoring Receptor in Patients with Acquired Hypoparathyroidism" J. Clin. Invest. 97(4):910–914.

PARATHYROID CYTOSOLIC AUTOANTIGENS RECOGNIZED BY AUTOANTIBODIES FROM PATIENTS WITH ACQUIRED HYPOPARATHYROIDISM

CROSS-REFERENCE TO A RELATED APPLICATION

This application is a division of Ser. No. 08/519,905, filed Aug. 28, 1995 (now U.S. Pat. No. 5,723,343).

The work associated with this invention was supported by grants from Genetech Foundation for Growth and Development (94-338), the American Diabetes Association (Mentor Award), and National Institutes of Health (RO1 HD 19469). The government has certain rights in this invention.

BACKGROUND OF THE INVENTION i. Field of the Invention

This invention relates to autoantibodiesassociated with acquired hypoparathyroidism, the autoantigens recognized by these autoantibodies, and to assay methods useful in the detection and treatment of acquired hypoparathyroidism.

ii. Background

Acquired hypoparathyroidism(AH) results from a deficiency of parathyroid hormone (PTH) secretion which leads to hypocalcemia. PTH plays an important role in calcium homeostasis, in that it can enhance calcium resorption from bone, increase calcium reabsorption from the kidney, and act on the renal tubule to promote the conversion of 25-hydroxyvitamin D to its active 1,25-dihydroxy metabolite, which in turn, increases the intestinal calcium absorption (Conklin, 1994; Lund, 1980). The most prominent clinical features of hypocalcemia are muscular irritability, tetany and seizures (Aurbach, 1990).

AH occurs as a common component of type I autoimmune polyglandular syndrome (APS I) which presents in infants or young children. AH also occurs in association with Hashimoto thyroiditis and/or hypothyrodism, a combination which most often affects adult women. APS I is characterized by mucocutaneous candidiasis, hypoparathyroidism and Addison disease, often accompanied by early onset pernicious anemia, chronic active hepatitis, alopecia and primary hypogonadism (Neufeld, 1980; Neufeld, 1981; Winter, 1992, Maclaren, 1985; Muir, 1991). APS I occurs either as an autosomal recessive disease, or as a seemingly sporadic disorder. Whereas APS I is not linked to genes within the HLA-DR region (Ahonen, 1988), the responsible gene has been recently mapped to chromosome 21q22.3 (Aaltonen, 1994). AH may result in mental retardation or unexplained epilepsy if it is not appropriately recognized and treated by the relatively simple and inexpensive expedient of activated vitamin D therapy and calcium supplementation. In APS I, however, normalization of calcium levels through vitamin D supplements may be confounded by malabsorption.

An autoimmune etiology for AH has been suggested because of its association with other autoimmune diseases (Ahonen, 1990), and by reports of autoantibodies directed against the parathyroid tissues in affected individuals. Autoantibodies to the parathyroid glands were first reported by Blizzard et al (Blizzard, 1966). In that study, 38% of 74 patients with autoimmune hypoparathyroidism were found to be positive compared with only 6% of 245 healthy control subjects. The results from subsequent studies were controversial, since the antibodies often appeared to be directed against mitochondrial antigens. These may be false positive results, because mitochondrial rich cells are found within normal parathyroid tissue and anti-mitochondrial antibodies are common in autoimmune disorders (Betterle, 1985). Autoantibodies from the sera of patients with sporadic adult onset hypoparathyroidism however have been reported to bind to the cell surfaces of human parathyroid cells, resulting in an inhibition of PTH secretion (Posillico, 1986). In addition, autoantibodies in the sera of patients with AH have been reported to be cytotoxic for cultured bovine parathyroid cells, by an antibody mediated cytotoxicity dependent on complement fixation and activation (Brandi, 1986; Fattorossi, 1988). Whereas the above findings may suggest the possible involvement of autoantibodies against parathyroid glands in AH, the nature of the targeted autoantigens has only recently been identified by Song et al., Abstract No. OR2-3, 77th Annual Meeting of the Endocrine Society, Washington, D.C., Jun. 14–17, 1995.

The regulation of PTH secretion requires that parathyroid cells sense the serum free ionized calcium levels in extracellular fluid. The recently cloned calcium sensing receptor (CA-SR) responds to increased levels of extracellularcalcium by triggering a phospholipase-C (PLC) dependent pathway which in turn induces the parathyroid cell to decrease its constituent PTH secretion (Conklin, 1994). The CA-SR gene has been mapped to chromosome 3q2 (Pollak, 1993), and the translated protein is a linear peptide of 1085 amino acids, with 7 putative transmembrane-spanningdomains and a large extracellular domain of 613 amino acids at the amino terminus (Brown, 1993). The external domain probably serves as the actual ionized calcium detector. It is a member of a new family of G-protein-coupled receptors which is densely expressed in parathyroid cells, but to some extent also in thyroid C-cells, brain and kidney. Mutations of the CA-SR gene have been found to be responsible for familial benign hypocalciuric hypercalcemia (FBHH) and autosomal dominant hypocalcemia (Pollak, 1993).

The following references are discussed in greater detail below:

1. Betterle, C., et al. (1985) *Clin. Exp. Immunol.* 62:353–360.
2. Blizzard, R. M., et al. (1966) *Clin. Exp. Immunol.* 1:119–128.
3. Brandi, E. M., et al. (1986) *P.N.A.S. USA* 83:8366–8369.
4. Brown, E. M., et al. (1993) *Nature* 366:575–580.
5. Fattorossi, A., et al. (1988) *P.N.A.S. USA* 85:4015–4019.
6. Irvine, W. J., et al. (1969) *Clin. Exp. Immunol.* 4:505–510.
7. Juhlin, C., et al. (1987) *P.N.A.S. USA* 84:2990–2994.

None of these references teach or suggest that the autoantibodies detected in patients with AH have, as their antigenic target, the calcium sensing receptor expressed by parathyroid chief cells. In addition, none of these references make any mention of the 70 or 80 kilodalton proteins which are part of the instant invention.

The Blizzard reference noted the existence of antibodies in patients with hypoparathyroidism which seemed to react in an organ specific manner with parathyroid tissue. The reactive antigen was not identified, and the authors cast doubt on whether such autoantibodies could have any etiologic relationship to the development of AH. Thus, Blizzard et aL teach away from the instant invention which establishes such a relationship. It is noted, however, that Blizzard et al make reference to publications of Davis, et al. (Lancet ii, 1432, 1961) and of Jones & Fourman (Lancet ii, 119, 1963; Lancet ii, 121, 1963), in support of the suggestion that "a test to detect subclinical hypoparathyroidism . . . would permit detection of partial hypoparathyroidism." The assay method of the instant invention is different from the test taught in those references.

The Irvine reference reported the presence of antibody which reacted with both parathyroid oxyphil and chief cells in a patient with idiopathic hypoparathyroidism. However, the identity of the antigens involved in those immune responses was not determined.

The Betterle reference suggests the existence of anti-mitochondrial autoantibodies in idiopathic hypoparathyroidism, and takes exception to Blizzard et al.'s suggestion that the autoantibodies detected in AH are parathyroid organ specific. The antigen identified by Betterle et al. was a 46 kilodalton protein, clearly different from the antigens identified in the instant invention.

The Brandi et al. reference discloses an antibody in AH patients which was cytotoxic for parathyroid and adrenal cortex cells, but not for pituitary, thyroid, liver or kidney cells. The assay method disclosed depends on cell culture and cytolysis (release of $^{51}Cr$) or immunofluorescence. The antigens involved in the method are not identified. Thus, a specific antigen based assay method is neither disclosed nor suggested.

The Juhlin reference relates to the development of monoclonal antibodies against whole parathyroid cells which exclusively recognize antigens on parathyroid and kidney tubule cells. The authors speculate that the antibodies bind to and block a cell surface calcium sensing receptor on these cells. However, the antibodies used in the study were not autoantibodies, and the nature of the antigen recognized was not defined, other than speculatively, based on the functional changes observed upon antibody binding.

The Fattorossi reference is a follow-up and an extension of the work reported by Brandi et al. The cytotoxic antibody was further classified as an IgM, it was found to not be organ specific, it reacted with endothelial cells, and these researchers found that two target antigens, one of molecular weight 200 kilodaltons and the other of 130 kilodaltons, were recognized. There is no suggestion that the target antigens are related to the parathyroid specific calcium sensing receptor.

The Brown reference discloses the cloning of a bovine parathyroid extracellular calcium sensing receptor having a molecular weight of about 120 kilodaltons. There is no suggestion that there is any relationship between this receptor and autoimmune hypoparathyroidism.

Several patent publications are also discussed below:

1. U.S. Pat. Nos. 5,053,491 and 4,864,020, issued to Cance et al., Washington University:

These patents relate to monoclonal antibodies specific for an antigen present on the surface of parathyroid tissue and are used to identify parathyroid tissue. The antigen is a 191 kilodalton protein (unreduced; reduced molecular weight is about 171 kilodaltons). By contrast, the instant method and compositions relate to antigens of 120 kD, 70 kD and 80 kD; and fragments thereof.

2. WO 88/03271 and related foreign equivalents, Juhlin et al.:

This patent publication is related to the above noted Juhlin scientific publication discussed above.

3. WO 94/28019 and related foreign equivalents, Juhlin et al.:

This patent publication relates to the work of Brown et al., discussed above, which disclosed cloning of the bovine calcium sensing receptor. This patent application relates to the cloning of the human calcium sensor, which they refer to as the calcium sensor protein, or CSP. The CSP clone is said to be useful for obtaining agonists/antagonists to the CSP and for obtaining antibodies to the CSP. The antibodies and agonists/antagonists so obtained are predicted to be useful in the treatment of a number of disease states including hyperparathyroidism. Thus, like the Brown et al. publication, this publication does not make any connection between the CSP and autoimmune hyparathyroidism. Of interest is the identification of this molecule by the WO 94/28019 applicants as having a molecular weight of 500 kDa. The instant invention, by contrast, relates to the human parathyroid calcium sensing receptor as a 120 kDa molecule.

4. U.S. patent application Ser. No. 07/356,999, U.S. Department of Health and Human Services, Aurbach:

This patent publication relates to the above discussed Brandi et al. and the subsequent Fattorossi et al. publications. This publication refers to a bovine parathyroid cell line in culture which, it is urged, is useful for the characterization of the antibody in autoimmune hypoparathyroidism. A specific antigen based assay method is neither taught nor suggested.

In the paragraph bridging pages 17 and 18 of the reference, it is postulated that the availability of a clone for the 500 kDa protein may assist in studies of autoimmune hypoparathyroidism. A publication of Brown, E. M. (1991) *Phys. Rev.* 71, 371–411 is cited as implicating autoimmunity in the pathogenesis of rare idiopathic hypoparathyroidism.

By contrast of the above discussed references this invention documents the existence of parathyroid autoantibodies in AH, and characterizes the reacting human specific parathyroid autoantigens. The parathyroid reactive autoantibodies are frequent in AH, and the CA-SR is an important autoantigen target in the disease.

Our finding that parathyroid cell derived CA-SR is a major autoantigen in AH targeted by autoantibodies is a novel observation, adding to the list of autoantigens that are receptors targeted by an immune response in an organ specific autoimmune disease (Wilkin, 1990). The thyroid stimulating hormone (TSH) receptors in autoimmune thyroid disease (Davies, 1981), acetylcholine (ACh) receptors of skeletal muscle in myasthenia gravis (Gonzalez-Ros, 1984; Fumagalli, 1982; and Aesonki, 1981), gastrin receptors in pernicious anemia (Loveridge, 1980), corticotropin receptors in Addison disease (Kendall-Taylor, 1988), and insulin receptors in IDD (Maron, 1983) are important autoantigens to their respective diseases. The mechanisms for involvement of receptors in autoimmune responses are probably complex. The first possibility is that autoantibodies against cell-surface receptors may lead to functional abnormalities of the cells expressing them, resulting in receptor-mediated stimulation or inhibition of the targeted cells. One example of stimulation by an agonist autoantibody mimicking a physiologic molecule is Graves disease which is caused by the binding of autoantibody to TSH receptors such that they are stimulated but in a more prolonged manner than for TSH itself (long acting thyroid stimulator or LATS). One example of inhibition by antagonist autoantibody is myasthenia gravis which is caused by the binding of antibody to ACh receptors. The second possibility is that the autoantibodies cross-link the receptors and increase the rate of their degradation which ultimately lead to their depletion. The third possibility is that the autoantibody can bind to the receptor, fix complement, and thereby induce damage to the cells expressing the receptor. In our study, the autoantibody directed against the external domain of the CA-SR may play a direct role in the pathogenesis of AH as an agonist autoantibody. The autoantibody could induce the same effect as normal serum ionized calcium by binding and activating the receptors which in turn stimulate signal transduction events thereby raising intracellular ionized calcium levels and depressing PTH secretion. That we found the external domain and not the internal domain of the CA-SR to contain the reactive epitope of parathyroid autoantibodies in AH, suggesting a functional role for the autoantibodies. This is also supported by a previous report that autoantibodies from the sera of patients with adult-onset AH bound to the cell surface of human parathyroidcells and induced inhibition of PTH secretion (Posillico, 1986). Alternatively, the autoantibodies could directly induce damage to the PTH-secreting cells. This is consistent with other reports that autoantibodies in the sera of patients with AH were found to be cytotoxic to cultured bovine parathyroid cells by an antibody mediated cytotoxicity (Brandi, 1986; Fattorossi, 1988), and that the epithelial cells of the parathyroid glands in AH patients were either diminished in number or absent by histological studies, sometimes accompanied by a lymphocytic infiltrate. T cells may be contributors to the pathogenesis of AH (Wortsman, 1992), however, we conclude that AH may be predominantly an antibody-mediated disease for which the instant detection and treatment method provides a significant solution.

BRIEF SUMMARY OF THE INVENTION

Acquired hypoparathyroidism (AH) has been considered to result from an autoimmune process, but the targeted self-antigens have only recently been identified. This invention discloses our study which included 25 patients with AH, of which 17 had type I autoimmune polyglandular syndrome and 8 were associated with autoimmune hypothyroidism. Autoantibodies were sought against antigens in hyperplastic human parathyroid glands using an immunoblotting assay. We discovered that twelve of 17 (70%) AH sera that we tested reacted to a cytosolic antigen of 70 kDa, and 16 (94%) to one of 80 kDa. Four of 20 (20%) AH sera also reacted to a membrane associated antigen of 120–140 kDa, the exact size of the calcium sensing receptor (CA-SR) dependent upon its degrees of glycosylation. None of the sera from 50 patients with autoimmune diseases other than AH or 22 normal disease-free controls had such parathyroid autoantibodies. Six of 20 (30%) sera from AH patients reacted to the CA-SR transfected on HEK-293 cells while 14 of all 25 (56%) AH sera reacted to external domain (60–70 kDa) of the CA-SR translated in vitro by a rabbit reticulocyte expression system. These discoveries confirm the role of the antigens in the pathogenesis of AH.

The findings of parathyroid specific autoantibodies in many patients with AH document the autoimmune nature of this disease, while the localization of the reactive epitope of the CA-SR to its external domain suggests that activation of the receptor could induce inhibition of PTH secretion in the disease.

This invention is a method useful in the detection of autoantibodies in persons that have developed, or are at risk of developing AH. The specific targets of autoantibodies associated with this disease are identified as: (1) the extraccliular portion of the calcium sensing receptor which has a total molecular weight of about 120–140 kilodaltons, expressed on the surface of chiefcells of the parathyroid; and (2) two additional, cytosolic antigens, one having a molecular weight of about 70 kilodaltons, and the other having a molecular weight of about 80 kilodaltons. It is noted that a higher percentage of AH antisera react with the 70 or 80 kilodalton proteins than with the 120–140 kilodalton receptor protein. One utility of this invention is that the identified autoantigens, or antigenic fragments thereof, may be used to achieve early diagnosis and treatment of AH, and possibly other autoimmune diseases which are frequently associated with AH.

Accordingly, one object of this invention is to provide a method for detecting autoimmune hypoparathyroidism in a patient, or propensity for developing autoimmune hypoparathyroidism and the propensity to develop other autoimmune diseases which are commonly associated with development of autoimmune hypoparathyroidism.

Another object of this invention is to provide a method for detecting autoimmune hypoparathyroidism related autoantigens.

Another object of this invention is to provide a method for obtaining isolated polynucleotide which encodes an autoimmune hypoparathyroidism related autoantigen.

Another object ofthis invention is to provide a method for making a recombinant cell transfected with an isolated polynucleotide which encodes an autoimmune hypoparathyroidism related autoantigen.

Another object of this invention is to provide a method for treating patients with autoimmune hypoparathyroidism or those at risk of developing autoimmune hypoparathyroidism.

DETAILED DESCRIPTION OF THE INVENTION

Figure 1:
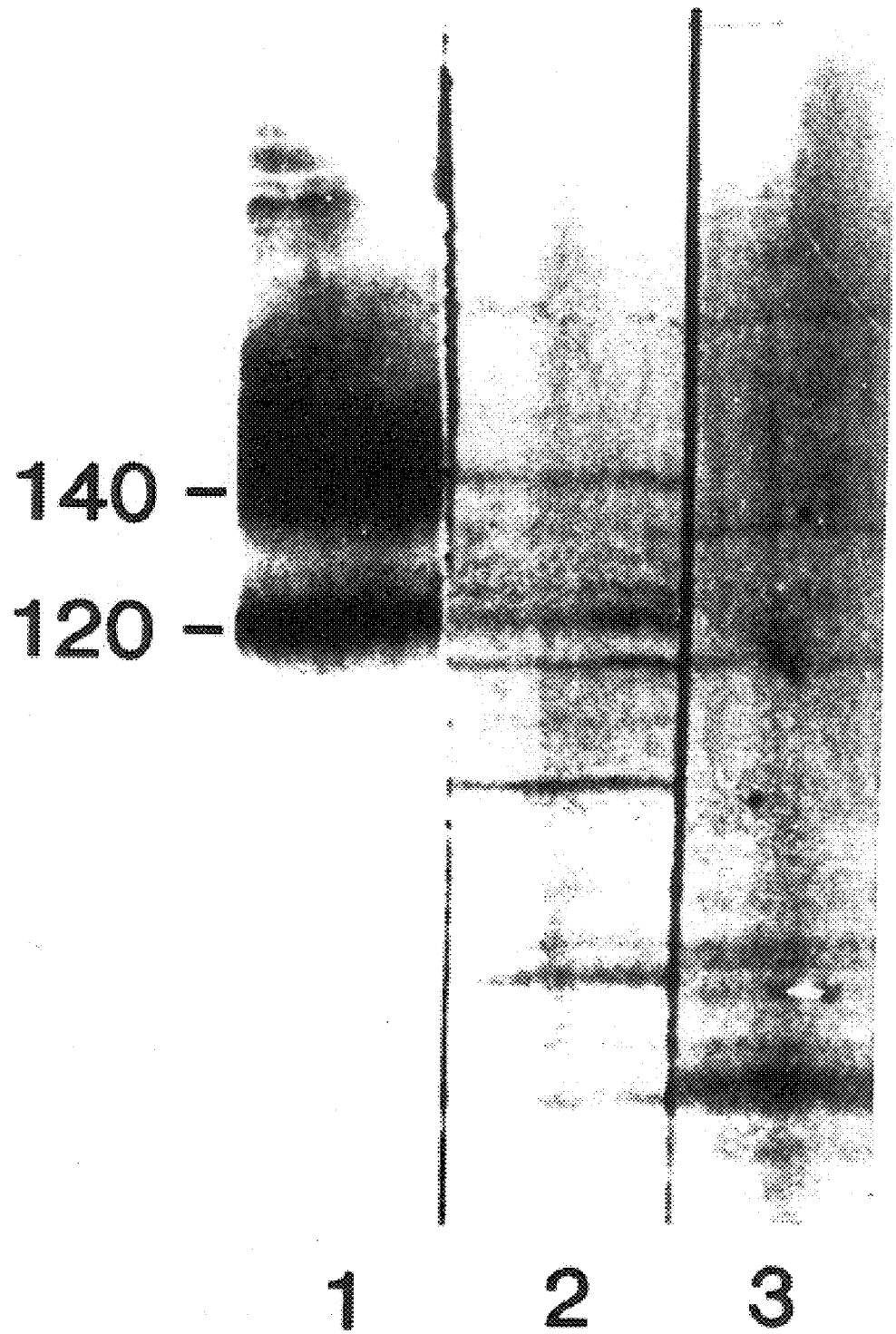
FIG. 1—Immunoblotanalysis using membranes of HEK-293 cells transfected with human CA-SR cDNA. Immobilon strips containing the antigens were incubated with IgG of rabbit anti-CA-SR Ab (lane 1), AH patient sera (lane 2) and normal human sera (lane 3).

As the examples which follow demonstrate, our studies confirm the autoimmune nature of acquired hypoparathyroidism (AH) and demonstrate that autoantibodies in patients with AH target human parathyroid proteins of 70, 80 and 120–140 kDa. The autoantigens are disease-specific since they were only recognized by the sera from patients with AH and not from those with other autoimmune diseases. In addition, the autoantigens are tissue-specific since they were not detected by immunoblotting using cultured human melanocytes or rat pituitary cells as antigen sources. The autoantigens are not mitochondrial proteins, because we were careful to remove the mitochondrial proteins by centrifugation prior to immunoblotting in our studies. Furthermore, we chose fresh human hypercellular parathyroid glands and normal dog parathyroid glands instead of parathyroid cell lines or tumors, so that we could avoid spurious identification of any antigens that are not normally present in the parathyroid glands. The 120–140 kDa protein is the calcium sensing receptor CA-SR.

Using an immunoblotting assay and sera from 25 patients with AH, we discovered that 12/17 (70%) of the sera reacted with a 70 kDa antigen in the cytosol of the parathyroid, while 16/17 (94%) reacted with an 80 kDa antigen in the cytosol of the parathyroid. Four out of twenty sera (20%) reacted with a 120–140 kDa membrane associated antigen which we confirm to be the calcium sensing receptor or CA-SR, by reaction of these sera with cloned and expressed CA-SR.

Of interest, most of the CA-SR autoantibody positive patients (including 4 AH in the context of APS I and all 8 adult-onset AH in association with thyroid disease) were females. This finding is consistent with findings in other autoantibody mediated receptor-targeted diseases which occur predominantly in females. Four of our adult-onset AH patients developed their disease and had the CA-SR autoantibodies detected after they had babies, another 2 adult-onset AH patients developed their disease after menopause, while one who presented with AH in the context of APS I began her disease at the onset of her menses. This suggests a possible influence of female hormones in the etiology of the disease.

That autoantibodies to CA-SR were absent from some AH in the context of APS I patients could be explained by the complete loss of the autoantigen needed to drive their formation before they could be studied. Two of the CA-SR autoantibody negative AH1 patients had developed their disease 32 years prior to the study, while another 2 autoantibody negative AH patients developed their diseases more than 10 years prior to the study. A general characteristic of all autoimmune diseases is that there are remissions and exacerbations of the underlying pathogenic processes involved over time. With insulin dependent diabetes (IDD), islet cell autoantibodies (ICA) disappear following clinical onset of disease when the pancreatic β cells are destroyed, and, as a result, the ICA reactive self antigens have disappeared. AH may be no exception. Thus, some of our patients affected by AH undoubtedly had CA-SR autoantibodies at an earlier time point in their disease but had lost them before we could study them. Finally, although the Western blot technique can be used and is specific for antigen reactivity, it is a relatively insensitive method for detecting autoantibodies. Other more sensitive assays, such as radioimmunoassay or ELISA, are able to increase the autoantibody detection frequencies (Song, 1994), and are therefore preferred.

Interestingly, 8 adult-onset AH patients in our study were associated with autoimmune hypothyroidism. Since the CA-SR transcripts have also been detected in the thyroid glands by Northern blots (Brown, 1993), an autoimmunity directed to the CA-SR could account for the involvement of both organs. Thus, the detection method and treatment methods disclosed herein are applicable to AH as well as hypothyroid related pathologies. One male AH in the context of APS I had high titers of CA-SR autoantibody in addition to thyroid microsomal and thyroid thyroglobulin autoantibodies. In contrast, the autoantibodies to CA-SR were not detected from the 8 sera from age, sex and ethnicity matched control patients with hypothyroidism alone. Therefore, additional local events may be required to allow the development of an immune response to the CA-SR. Furthermore, the autoantibodies to CA-SRs on the parathyroid gland could be the initial phenomenon leading to PTH deficiency, followed by autoantibody reactivity to the CA-SRs on the thyroid glands and their subsequent involution through an immune mediated destruction.

The CA-SR appeared as 120–140 kDa bands on our immunoblots, and the external domain of the CA-SR appeared as 60–70 kDa bands on immunoprecipitation, due to differential glycosylation of the receptor components. However, this differential glycosylation did not appear to affect the antigenic structure of the CA-SR since both the 120–140 kDa and 60–70 kDa bands were well recognized by both the rabbit antibody and the AH patient sera. HEK-293 cells transfected with CA-SR contain more CA-SRs than normal human parathyroid gland membrane preparations. This may explain why more of the AH patients we studied were found to be positive when CA-SR transfected HEK-293 membranes, rather than human parathyroid gland membranes, were used as antigen sources in immunoblotting. In addition, we found that the in vitro translated external domain of CA-SR had much less background than the transfected HEK-293 cells and this may explain why as many as 56% of the AH patients we tested, many of whom had long-standing AH, were found to be positive when in vitro translated external domain of CA-SR was used as the antigen source in immunoprecipitation studies.

We have confirmed that the 70 and 80 kDa parathyroid protein antigens are not related to parathyroid secretory protein (PSP), which has a molecular weight of 70 kDa and is co-stored and co-secreted with PTH in the parathyroid gland (Leiser, 1989). That protein has been shown to be present in the secretory granules of a variety of neuroendocrine and endocrine tissues with greatest abundance in parathyroid glands and adrenal medulla. However, in tests using AH positive sera, PSP produced using an in vitro translation based immunoprecipitation technique revealed no positive reactivities.

In view of the above disclosure and the examples and further disclosure which follows, it will be obvious to those skilled in the art that our finding of autoantibodies to the CA-SR and to the 70 and 80 kDa parathyroid specific antigens in AH patients give rise to a valuable diagnostic test for the disease. Positive test results in the diagnostic test, described in detail below, indicates the need to initiate a regimen of compensatory calcium, activated vitamin D therapy, immunotherapy, or a combination of these therapies.

The diagnostic test of this invention is a method for detecting autoimmune hypoparathyroidism in a patient, or the propensity for developing autoimmune hypoparathyroidism and the propensity to develop other autoimmune diseases which are commonly associated with development of autoimmune hypoparathyroidism, such as hypothyroidism. The method comprises detecting the presence of serum antibodies which react with the human calcium sensing receptor (CA-SR), or antigenic subportions thereof, or which react with parathyroid specific cytosolic antigens which are associated with autoimmune hypoparathyroidism.

The method may use the entire CA-SR or merely the antigenic subportion of the human calcium sensing receptor, such as the external domain of the receptor. A source of parathyroid cell membranes expressing the CA-SR, or a membrane preparation from recombinant cells expressing the CA-SR is obtained according to methods well known in the art using the known sequence of the CA-SR (see materials and methods below) and may be used in the method.

Alternatively, or in addition, the method may utilize the purified or cloned, expressed and purified 70 kilodalton or 80 kilodalton cytosolic antigen present in parathyroid cells. These proteins are easily purified according to methods well known in the art, such as by preparing an affinity column to which is immobilized antiserum from an AH patient which is known to react with these cytosolic proteins. By preparing another column from an AH negative patient's serum, all proteins other than the 70 kDa or 80 kDa proteins may be adsorbed out of a cytosolic parathyroid preparation. The flow-through of this first column is then passed over the AH serum column, and the bound, purified antigens eluted by reducing pH or by other means well known in the art of immunoaffinity chromatography. As a final polishing step and to separate the 70 kDa from the 80 kDa protein, a size exclusion column or reversed phase HPLC column is run. The resulting isolated antigens may be used directly in the diagnostic method of this invention.

Alternatively, according to methods well known in the art, the proteins may be subjected to amino acid analysis and the amino acid sequence thereby derived used to design oligonucleotide probes for cloning the genes encoding these proteins. This is accomplished by screening either a human genomic library, or a human parathyroid cDNA library, both of which are commercially available or which may be prepared according to methods well known in the art (see Maniatis et al., Cold Spring Harbor, *Molecular Cloning*, 1982). Once identified, clones of the 70 and 80 kilodalton encoding nucleic acid sequences are isolated by restriction digestion and subcloned into an expression vector appropriate for expression of the encoded antigens in any given recombinant cell of choice, including but not limited to bacterial cells, yeast cells and mammalian cells. Those skilled in the art are well aware of the need to provide appropriate transcriptional initiation and termination signals and the need to provide appropriate translation start and stop codons. In addition, the nucleic acids encoding the 70 or 80 kDa parathyroid cytosolic antigens may be modified to adapt the coding sequences for optimal expression in the cell type chosen, such as by optimization of codon usage to match that of highly expressed proteins in that cell type.

Once expressed, the recombinant proteins may be recovered and isolated in essentially the same manner described above for the isolation of the naturally occurring antigens, with minor modifications based on the specifics of the recombinant cell type in which the antigen was expressed. The isolated antigens may then be used to generate a supply of antibodies, including monoclonal antibodies, according to known methods, which recognize the 70 or 80 kilodalton proteins. These antibodies may be used, for example, in the assay method described below. The 70 and 80 kDa antigens may also be labeled, with a radioactive tag, a fluorescent tag, an enzyme such as horse radish peroxidase, with avidin, with biotin, or any of a number of other known labels, such that competition experiments may be performed using the labeled antigens.

Once an adequate source of CA-SR rich membranes or antigenic portions of the CA-SR and/or 70 and 80 kDa parathyroid antigens is assured, either by isolation of the natural proteins or by recombinant expression as described above, the diagnostic test of this invention may be performed as follows.

Serum is isolated from a patient suspected of having autoimmune hypoparathyroidism or for whom it is important to rule out this possible condition.

The serum is reacted with membranes rich in CA-SR or with the isolated 70 and 80 kDa proteins and the interaction is quantitated by any of a number of methods known in the art. Thus, for example, the presence of AH specific autoantibodies is detected by contacting the patients' serum with biotin labeled AH antigen (70 kDa protein, 80 kDa protein, CA-SR membranes, or antigenic fragments thereof). The reaction is then contacted with a bead coated with immobilized avidin which reacts with the biotin on the AH antigen. If any antigen-antibody complex is formed, this is detected by contacting the beads with anti-human antiserum having a detectable label, such as a radioactive, fluorescent, enzyme or other moiety.

A similar detection assay may be run using CA-SR expressing membranes by, for example, first immobilizing the membranes(forexample on the surface of a microtiterplate), contacting the membranes with test serum, and then contacting the reaction with anti-human antiserum which is labeled as described above.

In addition to the above examples, the detection method may take the form of a western blot assay in which immobilized antigen is reacted with test serum, which is then detected by contacting with labeled antiserum.

From the foregoing disclosure and experimental results it is evident that the CA-SR, the 70 kDa and 80 kDa proteins are major antigens in the pathogenesis of AH, and are thus valuable in the diagnosis and therapy of the disease. Autoantibodies to these proteins are useful in disease prediction both in non-AH relatives of patients affected by AH, as well as in the general population. Such antibodies will be detectable by radioimmunoassay using the isolated or recombinant proteins, peptides or antigenic fragments thereof, by depletion or D-ELISA and/or by ELISA or immunoprecipitationas outlined here. Baculo-viral based eukaryotic expression systems are likely to be preferred, to fold the proteins appropriately, and glycosylate the protein if this enhances the antibody binding ability. However, such expression systems as COS cells, yeast cells, and bacterial cells such as *E. coli* could be used for this purpose as those skilled in the art are readily able to appreciate.

Fluid-based immunoassays using the antigens and antibodies of this invention provide the greatest sensitivity to the method since autoantibodiesof relevance mostly react to their respective autoantigen through conformational rather than through linear epitopes. The RIA and D-ELISA methods are most useful in fulfilling these properties. Accordingly, the autoantigens identified herein can provide a chemically based assay giving greater precision, reproducibility, and specificity to identification of AH and susceptibility to AH.

In addition to providing the detection methods described above, our identification of the AH antigens provides a method for antigen mediated immunotherapy based upon the use of recombinant protein antigen as a therapeutic agent to restore immune tolerance in AH. Thus, a method of treating patients with autoimmune hypoparathyroidism or those at risk of developing autoimmune hypoparathyroidism which comprises:

(a) detecting the disease or propensity of developing the disease by screening the patient's serum for autoantibody to a 120–140 kDa antigen, the 70 kDa antigen, the 80 kDa antigen, or a combination of these antigens;

(b) treating patients positive in the test of step (a) either with
  (i) compensatory PTH therapy,
  (ii) antibodies raised against the auto-antibodies that recognize the antigens used in step (a),
  (iii) antigens of step (a) to restore immune tolerance to AH associated antigens, or
  (iv) a combination of treatments (i)–(iii).

Cellular responses, such as by proliferation or by cytokine elaboration after in vitro exposure to the AH autoantigens are also useful in disease prediction and treatment.

The autoantigen peptide derivatives thereof are used in antigen based therapies, including giving the antigens intravenously to induce anergy; deliberately immunizing against the antigen such as to induce an antibody response mediated by T helper-2 type lymphocytes to induce immunosuppressiveeffects on the pathogenic T helper-1 lymphocyte subset;

or orally fed antigen such as to induce anergy and suppressive effects. In the field of insulin dependent diabetes (IDD), intravenous $GAD_{65}$ antigens have been given in early life in NOD mice and shown to induce reductions in the degree of the inflammatory infiltrates or insulitis lesions and prevent the onset of hyperglycemia(Kauffman et al. Nature 1994:366:69–72). Subcutaneous immunizations by insulin and insulin B chains in incomplete Freunds adjuvant will prevent diabetes in NOD mice for prolonged periods without reductions in the insulitis lesions. The infiltrating cells however change their phenotype from ones that make large amounts of interferon gamma to ones that do not. Transfer of splenic lymphocytes from mice protected from diabetes in this way also convey protection for periods of up to a month. The intervention thus induces an active immunosuppressive effect and an insulitis lesion that is protective rather than destructive associated with a switch from Th1 to Th2 responses. Further, the effect must be beyond that merely involving autoimmunityto insulin, since beta cell destruction is arrested. The release of protective cytokines into the milieux of the islet must then also inhibit adjacent autoimmunity responses to other self-antigens through a bystander effect (Muir, Maclaren et al. J Clin Invest 1995:95: 628–634; Ramiya, Muir and Maclaren, Clin immunotherapy 1995:3:177–183.) Repeated feedings of defined autoantigens may also be used to inhibit ongoing autoimmune diseases. In the case of the NOD mice, this has occurred through orally administered insulin (Weiner et al. Natl Acad Sci USA 1991:88:10252–10256) as well as through the use of oral feedings of insulin and GAD (Muir, Maclaren et al. Diabetes/Metabolism Reviews 1994:9: 279–287). Accordingly, therapeutic methods employing AH autoantigens alone or in combination with other antigens provides a novel therapeutic approach to the treatment of AH which is expected to respond similarly to such treatment as outlined for the IDD studies noted above.

It should be noted that patients with other autoimmune diseases should be considered at-risk of developing or having AH, and should therefore be screened for AH autoantibody according to the methods described herein. Those patients found to be positive for the autoantibody, and their family members, should be considered for treatment according to the methods described herein. The reliable immunological assay of this invention can be automated or developed as a finger stick screening test. Furthermore, this invention provides a kit for detecting AH in a patient or in people at-risk of developing AH. The kit would contain any one or all of the following antigens: the CA-SR or antigenic subportions thereof, the 70 kDa protein, the 80 kDa protein. In addition, provision of animal anti-human immunoglobulin, especially if labeled, would allow immobilized antigen to be bound by AH autoantibody and then be detected by contacting the labeled animal anti-human immunoglobulin with the antigen-autoantibody complex.

MATERIALS AND METHODS a. Patients:

We examined sera from 25 patients with AH. Of these, 17 patients had APS I (all of them had AH, 14 had mucocutaneous candidiasis, 10 had Addison disease, many had associated vitiligo, alopecia, chronic active hepatitis and/or primary hypogonadism). Another 8 patients had adult-onset hypoparathyroidism associated with goiter and autoimmune hypothyroidism, confirmed by the presence of thyroid microsomal antibody and/or thyroglobulin antibody (Table 1):

TABLE 1

Characteristics of AH patients

| Subject | Number | Gender | Age of Onset (range) |
|---|---|---|---|
| AH in APS I | 17 | 10F & 7M | 1 yr–12 yr |
| AH in Adult | 8 | 8F & 0M | 31 yr–53 yr |

In addition, 8 age-matched and sex-matched adult-onset hypothyroidism patients who had normal calcium levels and no evidence of AH were used as controls. We also studied sera from 10 patients with Addison disease, 10 with Graves disease, 12 with Hashimoto thyroiditis, 10 with insulin dependent diabetes (IDD) and 8 with vitiligo (none of whom had AH ), as well as 22 normal disease-free controls. No normal controls had any endocrine-associated serum autoantibodies, such as thyroid microsomal, thyroglobulin autoantibodies, or islet cell autoantibodies.

b. Antigen Preparation

Hypercellular human parathyroid glands were obtained after their surgical removal from three patients being treated for hyperparathyroidismand osteomalacia, associated with renal failure. The parathyroid glands were placed on ice in phosphate-buffered saline (PBS,pH 7.4) with a mixture of protease inhibitors (1,10-phenanthroline, aprotinin, EDTA and benzamidine). The tissue was homogenized with a glass tissue grinder and centrifuged at 15,000×g to remove cell debris, nuclei and mitochondrial proteins. The supernatants were further separated into membrane and cytosolic fractions by ultracentrifugationat 100,000×g. Both the membrane and cytosolic fractions were used as antigen sources in immunoblot experiments.

Plasma membrane preparations from HEK-293 cells expressing the CA-SR together with membrane preparations from wild type HEK-293 cells were used as antigen sources in the immunoblotting and immunoprecipitation studies below.

c. Immunoblotting

The cytosolic and membrane fractions were solubilized in sodium dodecyl sulfate (SDS) gel loading buffer containing DL-dithiothreitol (DTT) and heated for 3 minutes at 100° C. before loading. After separation by SDS-PAGE, the proteins were transferred onto Immobilon-P membranes (Millipore, Bedford, Mass.). The strips of the membrane were cut and incubated with 1% BSA in Tris-buffered saline and 0.05% Tween-20 (TBST) to block free potential binding sites. Test sera at 1/100 dilutions as well as purified IgG of a rabbit anti-CA-SR antisera and IgG of pre-immune rabbit sera were incubated with the antigen-containing strips. The strips were then incubated with an anti-human or anti-rabbit polyvalent immunoglobulin alkaline phosphatase conjugate, and developed with 5-bromo-4-chloro-3-indolyl phosphate (BCIP) and nitro blue tetrazolium (NBT) (Promega, Madison, Wis.).

d. In vitro Translation and Immunoprecipitation

The CA-SR is a linear peptide of 1085 amino acids, with 7 putative transmembrane domains and a large extracellular domain of 613 amino acids at the amino terminus. The human CA-SR cDNA (Brown, 1993; Pollak, 1993) external and internal domains were amplified by polymerase chain reaction (PCR). The PCR products were positioned downstream of the SP6 promoter on the pcDNA3 construct. The recombinant plasmid was propagated in *E. coli* and purified by the Magic™ Minipreps System (Promega). The CA-SR cDNA was transcribed and translated as described according to the manufacturer's instructions. In brief, 1 μg circular plasmid DNA was transcribed in a 100 μl reaction for 2 hours at 40° C., using SP6 RNA polymerase (Stratagene, La Jolla, Calif.) in the presence of RNAsin (Promega). The translation was done using a methionine-free rabbit reticulocyte lysate in a 50 μl reaction using 20% of the synthesized RNA as a substrate in the presence of 4 μl $^{35}$S-methionine (10 mCi/ml) (Amersham, Arlington Heights, Ill.).

Once the translation reaction was complete, the translated products were examined by taking 5 μl aliquots mixed with 20 μl of SDS sample buffer. The samples were heated at 100° C. for 2 minutes and loaded to SDS-polyacrylamide gel (SDS-PAGE). For autoradiography, the gels were dried and exposed to X-ray film (XAR-2 ready pack, Sigma, St Louis, Mo.) overnight at room temperature. Since CA-SR is a glycoprotein, 1 μl of canine pancreatic microsomes (Promega) were added to the translation reaction mixture in order to obtain the mature glycosylated receptor.

For characterization of the autoantibody reactivities, 1 μl of the translated products were incubated with 2 μl of sera at 4° C. overnight. The immunocomplexeswere washed three times with ice-cold PBS and incubated with protein A—Sepharose beads for another 45 minutes. After washing, 50 μl of the SDS gel loading buffer was added to the bead and boiled for 2 minutes. Autoradiographies of the metabolically labeled proteins precipitated by antibody binding were performed as above.

Following are examples which illustrate procedures, including the best mode, for practicing the invention. These examples should not be construed as limiting. All percentages are by weight and all solvent mixture proportions are by volume unless otherwise noted.

Example 1—Characterization of Autoantibodies

Autoantibodies were detected against several parathyroid specific proteins in 17 AH sera that we tested by immunoblottingas described above. Twelve (70%) reacted to a protein of 70 kDa, and 16 (94%) to one of 80 kDa. The 70 and 80 kDa proteins were localized to the cytosolic fraction of the parathyroid extracts. Four of 20 sera (20%) so tested had autoantibodies which reacted with a doublet 120–140 kDa protein in the membrane fraction. Sera from 50 patients with other autoimmune diseases as well as 22 normal controls were also tested, and none of them reacted with any of the above specific parathyroid proteins (Table 2):

TABLE 2

Autoantibody reactivity to human parathyroid gland (immunoblot)

| Disease | Cytosolic | | Membrane |
|---|---|---|---|
| | 70 kDa | 80 kDa | 120–140 kDa |
| Hypoparathyroidism | 12/17 (70%) | 16/17 (94%) | 4/20 (20%) |
| Addison disease | 0/10 | 0/10 | 0/10 |
| Graves disease | 0/10 | 0/10 | 0/10 |
| Hashimoto thyroiditis | 0/12 | 0/12 | 0/12 |
| IDD | 0/10 | 0/10 | 0/10 |
| Vitiligo | 0/8 | 0/8 | 0/8 |
| Normal Control | 0/22 | 0/22 | 0/22 |

The autoantibodies were also detectable using a normal dog parathyroid gland as antigen source in immunoblotting. Flowever, they could not be detected using cultured human melanocytes or rat pituitary cells as antigen sources.

Example 2—Identification of the Autoantigens

Since the parathyroid 120–140 antigen has the same molecular weight as the CA-SR dependent upon its degree of glycosylation, we tested the possibility that the receptor itself was the autoantigen by three different experimental approaches.

In the first approach, the reactivities of rabbit anti-CA-SR IgG and patient sera were tested by immunoblotting using parathyroid gland membranes as the antigen source. The patient sera reacted to a 120–140 kDa protein, which closely matched that recognized by the rabbit anti-CA-SR IgG. Normal control sera and the same concentration of IgG from pre-immunized rabbit did not so react.

In the second approach, the reactivity of rabbit anti-CA-SR IgG and patient sera was examined using transfected HEK-293 cells as an antigen source in immunoblotting experiments. This cell line had been transfected with a human CA-SR cDNA. The patient sera again reacted to a 120–140 kDa protein, which closely matched that recognized by the anti-CA-SR IgG raised in rabbits (FIG. 1). Six AH patient sera (30%) reacted to the CA-SR from this source, but none of the 15 normal control sera did so. In addition, the 6 positive sera did not react to non-transfectedor wild type HEK-293 cells which did not express CA-SR proteins (Table 3):

TABLE 3

Autoantibody reactivity to recombinant Ca$^{2+}$-sensing receptor (immunoblot)

| Ag source | AH patients | Normal | Rabbit anti-CaR | Rabbit control |
|---|---|---|---|---|
| Transfected HEK-293 cell | 6/20 (30%) | 0/15 | + | − |
| Wild type HEK-293 cell | 0/6 | 0/10 | − | − |

Figure 2:
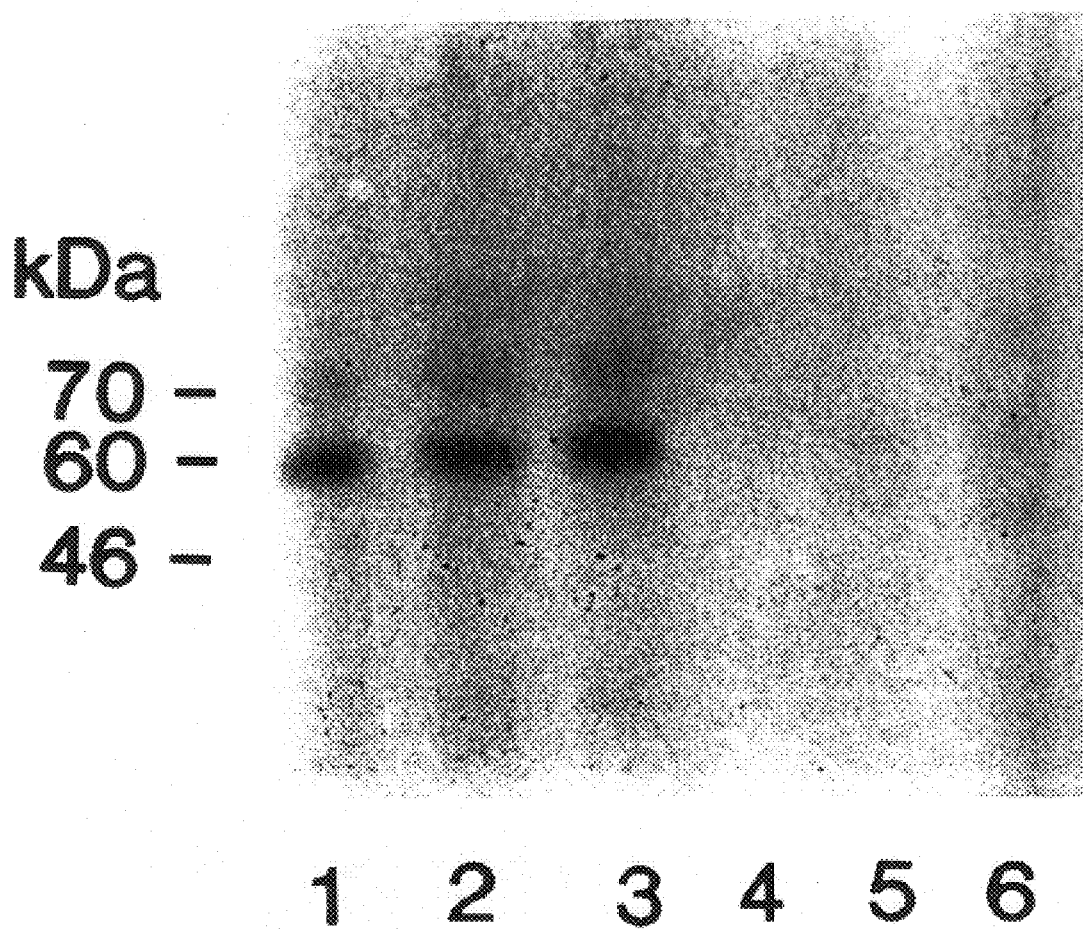
FIG. 2—Immunoprecipitation of the in vitro translated external domain of the CA-SR. In vitro translated products were incubated with AH patient sera (lane 1–lane 3) and normal human sera (lane 4–lane 6).

In the third approach, the localization of the antigenic epitopes was determined by immunoprecipitation of in vitro translated CA-SR antigen in lysate from a rabbit reticulocyte expression system. The patient sera reacted to both 70 kDa and 60 kDa proteins of the extracellular domain of the molecule, whereas no normal control sera did so (FIG. 2). The 60 kDa is the non-glycosylated form according to the size of the cDNA insert (1.6 kb) while the 70 kDa is the fully glycosylated form resulting from the addition of canine pancreatic microsome membranes.

The cytosolic domain was translated as a 60 kDa protein and no glycosylation occurred after exposure to the microsomal membranes as expected. None of the patient sera reacted with the cytosolic or intracellular domain of the CA-SR (data not shown). In summary, 14 (56%) of AH patient sera reacted to the extracellular domain of the recombinantly expressed CA-SR, whereas none of the 25 AH patient sera reacted to the intracellular domain of the molecule. The autoantibody frequencies might have been higher if newly diagnosed patients had been exclusively studied. None of the 22 normal control sera reacted to either domain of the CA-SR. (Table 4):

TABLE 4

Autoantibody reactivity to in vitro translated domains of calcium sensing receptor (immunoprecipitation)

| Ag source | AH patient | Normal |
|---|---|---|
| Ca$^{2+}$-R Extracellular | 14/25 (56%) | 0/22 |
| Ca$^{2+}$-R Intracellular | 0/25 | 0/22 |

Example 3—Isolation, Cloning and Expression of the 70 and 80 Kilodalton Autoantigens The purified or cloned, expressed and purified 70 kilodalton or 80 kilodalton cytosolic antigens present in parathyroid cells are obtained by preparing an affinity column. This is achieved by immobilizing antiserum from an AH patient known to react with these cytosolic proteins. Activated SEPHAROSE beads for this purpose are obtained from Pharmacia and reacted with the serum in a ratio of 1 gram beads to 10 mg serum. A second column is prepared in the same way, except that serum from an AH negative patient is used.

A cytosolic extract of parathyroid is prepared by homogenizing parathyroid gland, preferably fresh from a morgue, in a hypotonic solution containing a cocktail of protease inhibitors. The membranes and debris are removed by centrifugation at a minimum of 25,000 rpm for an hour, and the cytosolic supernatant decanted. All proteins other than the 70 kDa or 80 kDa proteins are adsorbed out of the cytosolic parathyroid preparation by passage of the extract over the column prepared with immobilized AH negative serum. The flow-through of this first column is then passed over the immobilized AH serum column, and the bound, purified antigens eluted by reducing the pH. TIhe affinity column eluate is then concentrated and subjected to size-exclusion HPLC to separate the 70 kDa from the 80 kDa antigen. The resulting isolated antigens may be used directly in the diagnostic method of this invention.

Alternatively, the proteins may be subjected to amino acid analysis and the amino acid sequence is used to design oligonucleotide probes for cloning the genes encoding these proteins. A human parathyroid cDNA library is screened and positive clones isolated. The clones are sequenced to confirm that they contain sequence encoding the 70 or 80 kDa proteins, and positive clones are subcloned such that the antigen coding sequence is placed in an expression vector, which is then transfected into mammalian cells and grown in culture.

Once expressed, the recombinant proteins are recovered and isolated in essentially the same manner described above for the isolation of the naturally occurring antigens.

Example 4—Assay for Detecting AH or Propensity for AH and Other Autoimmune Diseases CA-SR rich membranes and 70 and 80 kDa parathyroid antigens are contacted with serum from a patient suspected of having autoimmune hypoparathyroidism or for whom it is important to rule out this possible condition.

The presence of AH specific autoantibodies is detected by contacting the patients' serum with biotin labeled AH antigen (70 kDa protein, 80 kDa protein, CA-SR membranes, or antigenic fragments thereof). The reaction is then contacted with a bead coated with immobilized avidin which reacts with the biotin on the AH antigen. If any antigen-antibody complex is formed, this is detected by contacting the beads with anti-human antiserum having a detectable label, such as a radioactive, fluorescent, enzyme or other moiety.

Example 5—Therapeutic Method

In addition to providing the detection methods described above, our identification of the AH antigens provides a method for antigen mediated immunotherapy based upon the use of recombinantor purified protein antigen as a therapeutic agent to restore immune tolerance in AH. Thus, a method of treating patients with autoimmune hypoparathyroidism or those at risk of developing autoimmune hypoparathyroidism comprises:

(a) detecting the disease or propensity of developing the disease by screening the patient's serum for autoantibody to a 120–140 kDa antigen, a 70 kDa antigen, an 80 kDa antigen, or a combination of these antigen;

(b) treating patients positive in the test of step (a) either with
   (i) compensatory PTH therapy,
   (ii) antibodies raised against antibodies that recognize the antigens used in step (a),
   (iii) antigens of step (a) to restore immune tolerance to AH associated antigens, or
   (iv) a combination of treatments (i)–(iii).

The antigens are preferably provided in relatively small doses to avoid induction of anaphylaxis. The mode of administration may be by intravenous administration of the autoantigens or antigenic fragments or peptide thereof, to induce anergy of auto-reactive elements. The dosages and regimen of repeating such treatment is defined by routine clinical studies. In addition, the proteins and peptides may be used for subcutaneous immunizations to induce a switch from Th2 to Th1 responses or formation of blocking antibodies. Yet another alternative is oral administration to induce anergy and immunosuppressive effects on by-stander autoimmune responses.

In a preferred method of the subject invention, prevention or treatment involves the administration of autoantigens to the susceptible individual. AH, as disclosed herein, has an autoimmune etiopathogenesis. Various mechanisms have been proposed that would account for the beneficial value of administering autoantigens as a preventive treatment. In addition, it is also well known in the art that the administration of autoantigens can be used to induce immunological non-responsiveness,that is, specific tolerance of the antigen. See U.S. Pat. No. 5,114, 844; Nagler-Anderson et al. (1986) *Proc. Natl. Acad. Sci USA* 83:7443–7446; Miller et al. (1984) *Clin. Immunol. Immunopathol.* 31:231–240; Silverman et al. (1983) *J. Immunol.* 131:2651–2661; Michael (1989) *Immune Invest.* 18:1049–1054. The administration of the AH auto-antigens according to the subject invention can be done using procedures, formulations, and administration routes well known in the art. As one skilled in the art having the benefit of this disclosure would appreciate, the administration of the AH auto-antigens or peptides can be by, for example, parenteral, oral, intranasal, or by modification of the patient's genome to express an antigenic epitope.

Example 6—Kits for Assay of Autoantibodies Associated with Acquired Hypoparathyroidism A reagent kit can be provided which facilitates convenient analysis of sera samples using the antigens of the subject invention. Kits can be prepared which utilize recombinant or synthetically produced peptides to serve as an antigen for the autoantibodies. The principles and methods for ELISA and RIA technologies to detect antibodies are well-established.

As an example, for the ELISA assay, one such kit could comprise the following components:

1. One or more of the AH antigens of the subject invention;
2. Enzyme (e.g., peroxidase);
3. Conjugated animal anti-human immunoglobulin; and
4. Positive and negative controls.

The above kit could be modified to include 96 well plastic plates, colorimetric reagents, ELISA readers, blocking reagents, and wash buffers.

Also by way of example, for the RIA, one such kit could comprise the following components:

1. One or more of the AH antigens of the subject invention;

2. Wash buffers;
3. Polyethylene glycol;
4. Goat or sheep antihuman precipitating (second) antibodies; and
5. Positive and negative controls.

Either of the above kits may be modified to include any appropriate laboratory supplies.

In addition to the use of immunoprecipitation techniques, the subject invention can be practiced utilizing any other procedures which facilitate detecting the presence of AH auto-antibodies. For example, other immunological methods which can be used include enzyme linked immunosorbentassay (ELISA) and radioimmunoassay (RIA). The principles and experimental methods of these procedures are well known to those skilled in the art. The assays can be carried out rapidly and efficiently by the use of the natural or recombinant proteins which bind with the AH auto-antibodies. Both whole cell and cell lysate procedures are familiar to those working in this field and can be readily employed to detect the AH antibodies.

The amino acid sequence of the AH auto-antigens identified herein can be analyzed to ascertain immunologically reactive epitopes. These epitopes are amino acid sequences which will react immunologically with the auto-antibodies. These sequences can then be produced recombinantly. For recombinant production, the DNA coding for the epitopes is inserted into a vector which is then used to transform an appropriate host cell to express the desired amino acid sequence. Although bacteria, insects, yeasts, and mammalian cells could all serve as appropriate hosts, if protein folding is an important factor in the reactivity of the epitope, then an eukaryotic cell would be a preferred host.

Purified protein or lysate of the cells producing the protein could be used for the assays.

Also, an alternative to using the AH auto-antigens would be to use antibodies generated to the AH auto-antigens, otherwise known as an anti-antibody. This antibody would immunoprecipitate with the AH auto-antigens, and the detection could be carried out as described above.

It should be understood that the examples and embodiment described herein are for illustrative purposes only and that various modifications or changes in light thereof will be suggested to persons in the art and are to be included within the spirit and purview of this application and the scope of the appended claims.

REFERENCES

Conklin B. R., Bourne H. R. (1994) "Marriage of the flytrap and the serpent," *Nature* 367:22.

Lund B. J., Sørensen OH, Lund B. I. et al (1980) "Vitamin D metabolism in hypoparathyroidism," *J. Clin. Endocrinol Metab* 51:606–610.

Aurbach G. D., Marx S. J., Spiegel A. M. (1990) "Parathyroid hormone, calcitonin, and the calciferols," In: J. D. Wilson, D. W. Foster, editors. *Williams textbook of endocrinology*, Philadelphia, W. B. Saunders 8: 1397–1476.

Neufeld M., Maclaren N. K., Blizzard R. (1980) "Autoimmune polyglandular syndromes," *Pediatr Ann* 9: 154–62.

Neufeld M., Maclaren N. K., Blizzard R. (1981) "Two types of autoimmune Addison disease associated with different polyglandular autoimmune (PGA) syndromes," *Medicine* 60: 355–62.

Winter W. E., Obata M., Maclaren N. K. (1992) "Clinical and molecular aspects of autoimmune endocrine disease," In: J. M. Cruse, R. E. Lewis Jr., editors. *Clinical and molecular aspects of autoimmune disease. Concepts Immunopathol.* Basel, Karger 8: 189–221.

Maclaren N. K., Riley W. J. (1985) "Thyroid, gastric, and adrenal autoimmunities associated with insulin-dependent diabetes mellitus," *Diabetes Care* 8(Supp 1):34–8.

Muir A., Maclaren N. K. (1991) "Autoimmune diseases of the adrenal glands, parathyroid glands, gonads and hypothalamic-pituitary axis," *Endocrinol Metab Clin North Am* 20: 619–44.

Ahonen P., Koskimies S., Lokki M. L., et al. (1988) "The expression of autoimmune polyglandular disease type I appears associated with several HLA-A antigens but not with HLA-DR," *J. Clin. Endocrinol Metab* 66: 1152–7.

Aaltonen J., Björses P., Sandkuijl L., Perheentupa J., Peltonen L. (1994) "An autosomal locus causing autoimmune disease: autoimmune polyglandular disease type I assigned to chromosome 21, " *Nat. Genet.* 8(1):83–7.

Ahonen P., Myllärniemi S., Sipilä I., Perheentupa J. (1990) "Clinical Variation of autoimmune polyendocrinopathy-candidiasis-ectodermal dystrophy (APECED) in a series of 68 patients," *N. Engl. J Med.* 322: 1829–36.

Blizzard R. M., Chee D., Davis W. (1966) "The incidence of parathyroid and other antibodies in the sera of patients with idiopathic hypoparathyroidism," *Clin. Exp. Immunol.* 119–128.

Betterle C., Caretto A., Zeviani M., et al. (1985) "Demonstration and characterization of anti-human mitochondria autoantibodies in idiopathic hypoparathyroidism and in other conditions," *Clin. Exp. Immunol.* 62:353–360.

Posillico J. T., Wortsman J., Srikanta S., Eisenbarth G. S., Mallette L. E., Brown E. M. (1986) "Parathyroid cell surface autoantibodies that inhibit parathyroid hormone secretion from dispersed human parathyroid cells," *J. Bone Miner Res.* 1:475–83.

Brandi M. L., Aurbach G. D., Fattorossi A., et al. (1986) "Antibodies cytotoxic to bovine parathyroid cells in autoimmune hypoparathyroidism," *Proc. Natl. Acad. Sci. USA* 83: 8366–8369.

Fattorossi A., Aurbach G. D., Sakaguchi K., et al. (1988) "Anti-endothelial cell antibodies: detection and characterization in sera from patients with autoimmune hypoparathyroidism," *Proc. Natl. Acad. Sci. USA* 85: 4015–4019.

Song, et al. (1995) Abstract OR2-3, 77th Annual Meeting of the Endocrine Society, Washington D.C., June 14–17.

Pollak M. R., Brown E. M., Chou Y. W., et al. (1993) "Mutations in the human $Ca^{2+}$-sensing receptor gene cause familial hypocalciuric hypercalcemia and neonatal severe hyperparathyroidism," *Cell* 75:1297–1303.

Brown E. M., Gamba G., Riccardi D., et al. (1993) "Cloning and characterization of an extracellular $Ca^{2+}$-sensing receptor from bovine parathyroid," *Nature* 366: 575–580.

Irvine, W. J., et al. (1969) "Antibody of the Oxyphil Cells of the Human Parathyroid in Idiopathic Hypoparathyroidism," *Clin. Exp. Immunol.* 4:505–510.

Juhlin, C., et al. (1987) "Monoclonal Antibodies with Exclusive Reactivity Against Parathyroid Cells and Tabula Cells of the kidney," *PNAS USA* 84:2990–2994.

Cance, et al., U.S. Pat. No. 5,053,491, issued Jan. 10, 1991.

Cance, et al., U.S. Pat. No. 4,864,020 issued May 9, 1989.

Juhlin, el al., WO 88/03271, published May 5, 1988.

Juhlin, et al., WO 94/28019, published Dec. 8, 1994.

Aurbah, U.S. patent application Ser. No. 07/356,999, published Aug. 29, 1989.

Wilkin T. J. (1990) "Receptor autoimmunity in endocrine disorders," *N. Engl. J. Med.* 8:1318–23.

Davies T. F. (1981) "Autoantibodies to the human thyrotropin receptor are not species specific," *J. Clin. Endocrinol. Metab.* 52: 426–30.

Gonzalez-Ros J. M., Ferragut J. A., Martinez-Carrion M. (1984) "Binding of anti-acetylcholine receptor antibodies inhibits the acetylcholine receptor mediated cation flux," *Biochem. Biophys. Res. Comm.* 120: 368–75.

Fumagalli F., Engel A. G., Lindstrom J. (1982) "Ultrastructural aspects of acetylcholine receptor turnover at the normal end-plate and in autoimmune myasthenia gravis," *J. Neuropathol. Exp. Neurol.* 41: 567–79.

Desouki A., Eldefrawi A. T., Eldefrawi M. E. (1981) "A new mechanism revealed for the action of antibodies on acetylcholine receptor function," *Exp. Neurol.* 73: 440–50.

Loveridge N., Bitensky L., Chayen J., et al. (1980) "Inhibition of parietal cell function by human gammaglobulin containing gastric parietal cell antibodies," *Clin. Exp. Immunol.* 41:264–270.

Kendall-Taylor P., Lambert A., Mitchell R., Robertson W. R. (1988) "Antibody that blocks stimulation of cortisol secretion by adrenocorticotrophichormone in Addison disease," *BMJ* 296: 1489–1491.

Maron R., Elias D., dejongh B. M. (1983) "Autoantibodies to the insulin receptor in juvenile onset insulin-dependent diabetes," *Nature* 303:817–818.

Wortsman J., McConnachie P., Baker J. R., Mallette L. E. (1992) "T-lymphocyte activation in adult-onset idiopathic hypoparathyroidism," *Amer. J Med.* 92:352–356.

Song Y. H., Connor E., Li Y., Zorovich B., Balducci P., Maclaren N. K. (1994) "The role of tyrosinase in autoimmune vitiligo," *Lancet* 344:1049–1052.

Leiser M., Sherwood L. M. (1989) "Calcium-binding proteins in the parathyroid gland," *J. Biolog. Chem.* 264:2792–2800.

What is claimed is:

1. A recombinant cell transfected with a polynucicotide encoding a 70 kD parathyroid cytosolic antigen which reacts with antibodies which are present in individuals with acquired hypoparathyroidism, but which are not present in individuals who do not have hypoparathyroidism.

2. A recombinant cell transfected with a polynucleotide encoding an 80 kD parathyroid cytosolic antigen which reacts with antibodies which are present in individuals with acquired hypoparathyroidism, but which are not present in individuals who do not have hypoparathyroidism.

3. An antigen expressed from a polynucleotide encoding a 70 kD parathyroid cytosolic antigen which reacts with antibodies which are present in individuals with acquired hypoparathyroidism, but which are not present in individuals who do not have hyporparathyroidism.

4. An antigen expressed from a polynucleotide encoding an 80 kD parathyroid cytosolic antigen which reacts with antibodies which are present in individuals with acquired hypoparathyroidism, but which are not present in individuals who do not have hvpoparathyroidism.

5. An isolated parathyroid cytosolic protein antigen having a molecular mass of about 70 kilodaltons, wherein said antigen binds with antibodies which are present in individuals with acquired hypoparathyroidism, but which are not present in individuals who do not have hypoparathyroidism.

6. An isolated parathyroid cytosolic protein antigen having a molecular mass of about 80 kilodaltons, wherein said antigen binds with antibodies which are present in individuals with acquired hypoparathyroidism, but which are not present in individuals who do not have hypoparathyroidism.

* * * * *

UNITED STATES PATENT AND TRADEMARK OFFICE
CERTIFICATE OF CORRECTION

Page 1 of 2

PATENT NO.   :   6,066,475

DATED        :   May 23, 2000

INVENTOR(S)  :   Noel K. Maclaren, Yao-Huo Song

It is certified that error appears in the above-identified patent and that said Letters Patent is hereby corrected as shown below:

Column 2, line 65: "et aL" should read --et al.--.

Column 3, line 58: "compositionsrelate" should read --compositions relate--.

Column 4, line 4: "antagoniststo" should read --antagonists to--.

Column 4, line 6: "antagonistsso" should read --antagonists so--.

Column 4, line 10: "hyparathyroidism." should read --hypoparathyroidism.-- .

Column 4, line 33: "parathyroidantoantigens" should read --parathyroid autoantigens--.

Column 5, line 12: "parathyroidcells" should read --parathyroid cells--.

Column 5, lines 60-61: "extraccliular" should read --extracellular--.

Column 5, line 63: "chiefcells" should read --chief cells--.

Column 6, line 20: "ofthis" should read --of this--.

Column 7, line 21: "negative AHl" should read --negative AH--.

Column 10, line 3: "membranes(for example" should read --membranes (for example--.

Column 10, line 30: "autoantibodiesof" should read --autoantibodies of--.

Column 11, line 19: "autoimmunityto" should read --autoimmunity to--.

Column 13, line 60: "Flowever" should read --However--.

UNITED STATES PATENT AND TRADEMARK OFFICE
CERTIFICATE OF CORRECTION
Page 2 of 2

PATENT NO. : 6,066,475

DATED : May 23, 2000

INVENTOR(S) : Noel K. Maclaren, Yao-Huo Song

It is certified that error appears in the above-identified patent and that said Letters Patent is hereby corrected as shown below:

Column 14, line 17: "non-transfectedor" should read --non-transfected or--.

Column 15, line 61: "recombinantor" should read --recombinant or--.

Column 17, line 38: "immunoprecipitatewith" should read --immunoprecipitate with--.

Column 17, line 44: "persons in the art" should read --persons skilled in the art--.

Column 18, lines 27-28: "Demonstrationand" should read --Demonstration and--.

Column 18, line 49: "hypercalcemiaand" should read --hypercalcemia and--.

Column 19, line 23: "dejongh" should read --deJongh--.

Signed and Sealed this

Fifteenth Day of May, 2001

Attest:

NICHOLAS P. GODICI

Attesting Officer        Acting Director of the United States Patent and Trademark Office